US00PP24640P3

(12) United States Plant Patent
Fleming

(10) Patent No.: US PP24,640 P3
(45) Date of Patent: Jul. 15, 2014

(54) ***ILLICIUM* PLANT NAMED 'JCJC'**

(50) Latin Name: *Illicium floridanum*
Varietal Denomination: JCJC

(75) Inventor: James Fleming, Newberry, FL (US)

(73) Assignee: Plant Development Services Inc., Loxley, AL (US)

( * ) Notice: Subject to any disclaimer, the term of this patent is extended or adjusted under 35 U.S.C. 154(b) by 271 days.

(21) Appl. No.: 13/385,496

(22) Filed: Feb. 21, 2012

(65) Prior Publication Data

US 2013/0219573 P1 Aug. 22, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Cassandra Bright

(57) ABSTRACT

A new and distinct *Illicium* cultivar named 'JCJC' is disclosed, characterized by rounded foliage, dark red flowers with a sweet fragrance. Plant form of the new cultivar is attractive, requiring little or no pruning. The new cultivar is a *Illicium,* suitable for ornamental garden purposes.

2 Drawing Sheets

Figure 1:
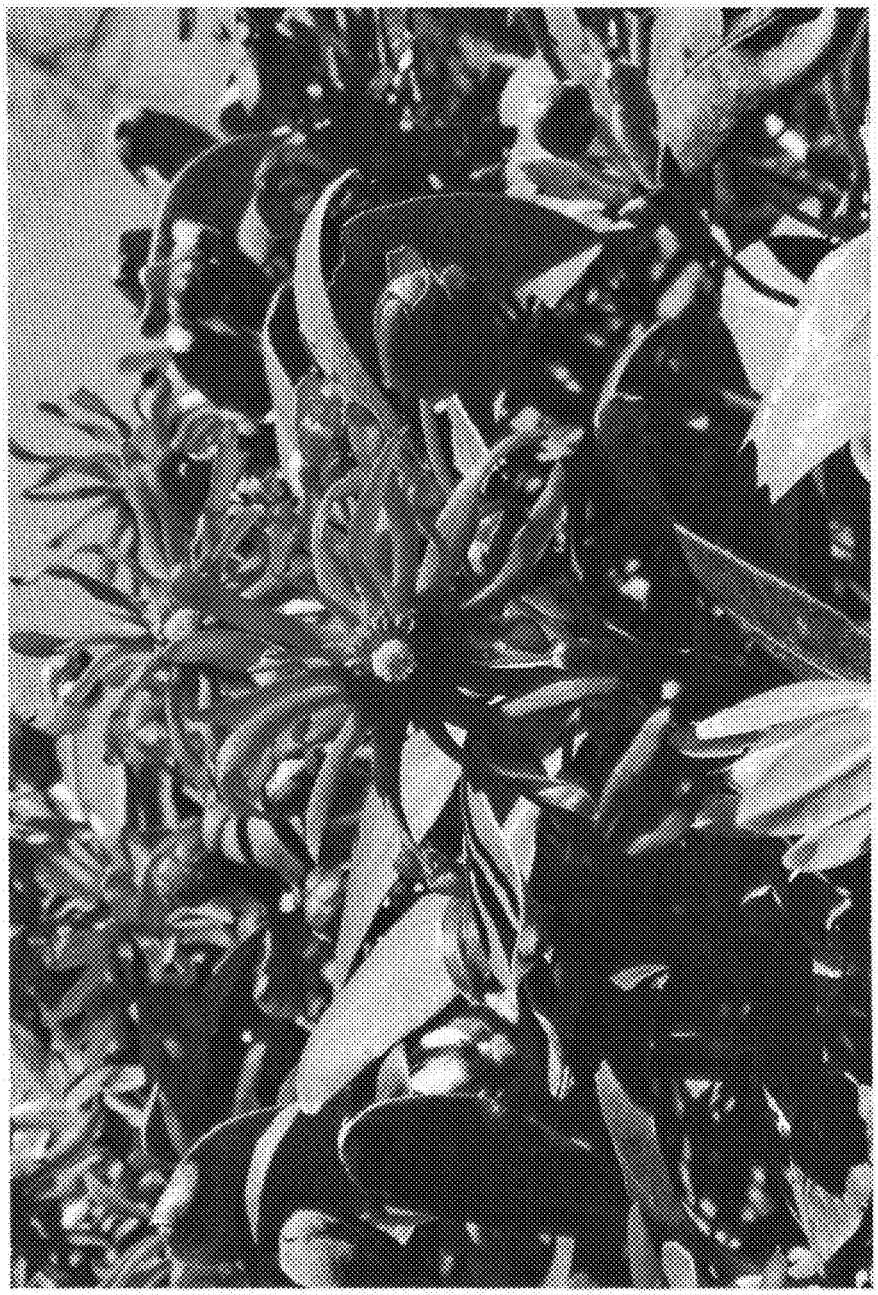

Latin name of the genus and species: *Illicium floridanum.* Variety denomination: 'JCJC'.

BACKGROUND OF THE INVENTION

The new cultivar is a product of a chance discovery in a commercial setting by the inventor. In approximately 1992 and 1994, the inventor, James Fleming collected seed of the native species, *Illicium floridanum.* The collected seed was planted at a commercial nursery in Newberry, Fla., and seedlings observed for interesting horticultural variations.

During the late 1990s the inventor noticed a seedling with an attractive plant shape and different leaf form. The seedling was then selected and propagated by semi-hardwood cuttings at the commercial nursery in Newberry, Fla. The initial propagation showed the plant to be stable and additional generations were propagated, also by semi-hardwood cuttings. Multiple generations have been reproduced since approximately 2000, and have shown that the unique features of this cultivar are stable and reproduced true to type.

SUMMARY OF THE INVENTION

The cultivar 'JCJC' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'JCJC' These characteristics in combination distinguish 'JCJC' as a new and distinct *Illicium* cultivar:

1. Unusual sweet fragrance
2. Dark red flowers
3. Attractive dense plant form, requiring little or no pruning
4. Rounded foliage.

COMPARISON TO PARENT VARIETY

Plants of the new cultivar 'JCJC' are similar to plants of the parent; *Illicium floridanum* in most horticultural characteristics, however, plants of the new cultivar 'JCJC' have foliage with a rounded shape. Additionally, plants of 'JCJC' produce darker red flowers with a sweet scent not found in the parent variety. Plant shape is improved in the new variety, forming attractive, dense plants that are less rangy than the parent.

COMMERCIAL COMPARISON

'JCJC' is best compared to the commercial variety *Illicium floridanum* 'Pink Frost' U.S. Plant Pat. No. 21,287. Plants of the new cultivar 'JCJC' are similar to plants of 'Pink Frost' in most horticultural characteristics, however, plants of the new cultivar 'JCJC' produce flowers with a unique sweet fragrance, compared to the malordorous fragrance of this 'Pink Frost'. Flower color of 'JCJC' is significantly darker than 'PinkFrost'.

'JCJC' can also be compared to the commercial variety *Illicium floridanum* 'Variegated *Illicium*' U.S. Plant Pat. No. 16,269. Plants of the new cultivar 'JCJC' are similar to plants of this comparator in most horticultural characteristics, however, plants of the new cultivar 'JCJC' have solid green foliage. Additionally, plants of 'JCJC' produce flowers with a unique sweet fragrance, compared to the fishy fragrance of this comparator. Flower color of 'JCJC' is significantly darker than this comparator.

BRIEF DESCRIPTION OF THE PHOTOGRAPHS

The accompanying photograph in FIG. 1 illustrates in full color a close up of typical foliage and flowers of 'JCJC' grown outdoors in Loxley, Ala.

Figure 2:
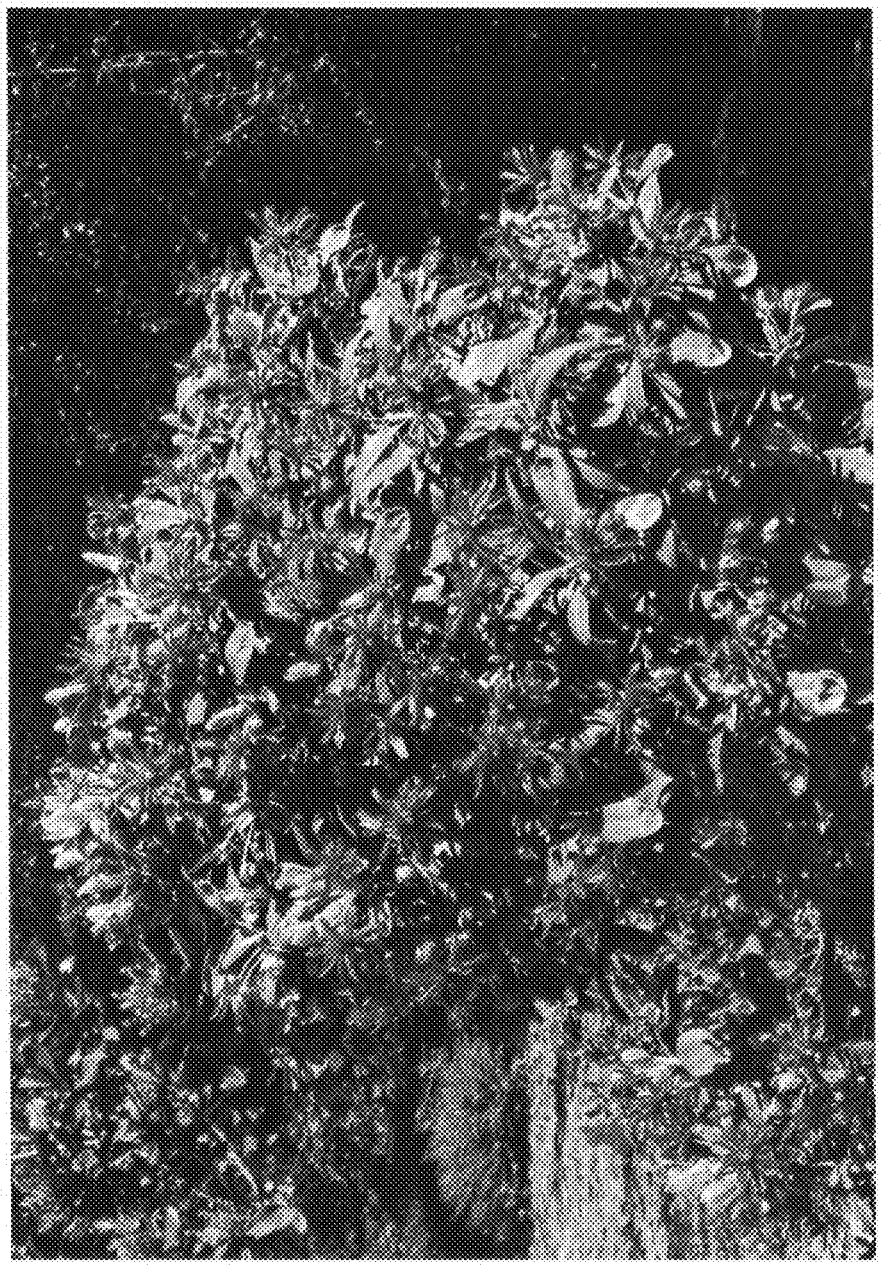

FIG. 2 illustrates in full color a typical plant of 'JCJC' grown outdoors in Alabama. The plant is approximately 5 years old, and is planted in the ground.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'JCJC' plants grown outdoors in Loxley, Ala. Plants are approximately 3 years old, in a 3 gallon nursery container. Measurements and numerical values represent averages of typical plant types.

Botanical classification: *Illicium floridanum* 'JCJC'.

PROPAGATION

Time to rooting: Approximately 6 weeks at approximately 32° C. from semi-hardwood cuttings.

Root description: Fine, fibrous young roots. Older roots becoming woody, colored near Grey-Brown 199C.

PLANT

Growth habit: Upright shrub. Moderately dense. Slow to moderate growth rate.

Height: Approximately 45 cm.

Plant spread: Approximately 60 cm. 10 year old mature plant is approximately 200 cm high by 150 cm wide.

Branching characteristics: Moderate branching, angled approximately 45° to 75°.

Length of lateral branches: Approximately 15 to 25 cm.

Number of lateral branches: Approximately 5 main lateral branches on a 3 year old plant.

Diameter of lateral branches: Approximately 1.2 cm.

Lateral branch strength: Very strong, with somewhat brittle.

Lateral branch color: Young branches near RHS Greyed-Green 197B. Mature branches near RHS Greyed-Green 195A.

Branch texture: Coarse. Irregular lenticels, colored Greyed-Orange 165B.

Number of leaves per lateral branch: Average 10 to 15.

Age of plant described: Approximately 3 years.

FOLIAGE

Leaf:

- *Type.*—Simple.
- *Arrangement.*—Pseudo-whorled, 5 to 7 per terminal whorl.
- *Average length*—Approximately 9 cm.
- *Average width.*—Approximately 4.5 cm.
- *Shape of blade.*—Obovate.
- *Apex.*—Obtuse, to occasionally semi-mucronate, with a small spicule attached to the underside of leaf, rather than at actual apex.
- *Base.*—Cuneate.
- *Attachment.*—Stalked.
- *Margin.*—Entire.
- *Texture of top surface.*—Smooth, leathery.
- *Texture of bottom surface.*—Smooth, leathery.
- *Foliage scent.*—Anise-like.
- *Color.*—Young foliage upper side: near RHS Green 137A. Young foliage under side: near RHS Green 137B. Mature foliage upper side: near RHS Green 139A, but darker. Mature foliage under side: near RHS Green 138A.
- *Venation.*—Type: Pinnate. Venation color upper side: Near RHS Yellow-Green 144B. Venation color under side: Near RHS Yellow-Green 144B.
- *Petiole.*—Length: Near 1.5 cm. Diameter: Near 0.4 cm. Color: Near RHS Yellow-Green 144B.
- *Stipule.*—Irregularly present. Length: Near 1.5 cm. Diameter: Near 0.4 cm. Margin: Ciliate. Shape: Deltoid. Color: Upper Surface: Near RHS Greyed-Orange 164A and 164B, both colors present. Under Surface: Near RHS Greyed-Orange 164C.

FLOWER

Bloom period:

- *Natural season.*—December to March in Georgia.

Flower:

- *Arrangement.*—Single star shaped flowers, occurring at leaf axils.
- *Diameter.*—Approximately 3.5 cm.
- *Depth.*—Approximately 3.0 cm.
- *Facing direction.*—Outwardly facing, at approximately 45° angle from stem attachment.
- *Persistent or self-cleaning.*—Persistent.
- *Fragrance.*—Sweet, pleasant.

Petals:

- *Length.*—Approximately 1.6 cm.
- *Width.*—Approximately 0.5 cm.
- *Apex.*—Blunt.
- *Shape of petal.*—Ovate.
- *Petal margin.*—Entire.
- *Petal arrangement.*—Radial, slightly overlapping.
- *Petal number.*—Average 25.
- *Petal texture.*—Smooth.
- *Color.*—Upper surface at first opening: Near RHS Red 53A. Under surface at first opening: Near RHS Red 53B. Upper surface at maturity: Near RHS Red-Purple 60A. Under surface at maturity: Near RHS Red-Purple 60A. Upper surface at fading: Near RHS Red-Purple 59A. Under surface at fading: Near RHS Red-Purple 59A.

Bud:

- *Shape.*—Oblong.
- *Length.*—1 to 1.5 cm.
- *Diameter.*—0.9 cm.
- *Color.*—Near RHS Red-Purple 59B.

Calyx/sepals:

- *Quantity per flower.*—5 sepals.
- *Shape.*—Spatulate.
- *Length.*—Average 1.0 cm.
- *Width.*—0.4 cm.
- *Apex.*—Obtuse.
- *Base.*—Attenuate.
- *Margin.*—Entire.
- *Texture.*—Smooth.
- *Color.*—Upper Surface: Near RHS Yellow-Green 145B and 145C, both colors present with a faint, irregular flush mainly along margins of Red-Purple 59C. Lower Surface: Near RHS Yellow-Green 145B and 145C, both colors present with a faint, irregular flush mainly along margins of Red-Purple 59C.

Peduncle:

- *Length.*—Average 1.1 cm.
- *Diameter.*—0.25 cm.
- *Color.*—Near RHS Yellow-Green 145B.
- *Texture.*—Glabrous.

Bracteoles:

- *Quantity per flower.*—Most commonly 2.
- *Shape.*—Deltoid.
- *Length.*—Average 1.1 cm.
- *Width.*—0.8 cm.

*Aspect.*—Strongly concave.
*Apex.*—Acute.
*Base.*—Cuneate.
*Margin.*—Entire.
*Texture.*—Smooth.
*Color.*—Upper Surface: Near RHS Yellow-Green 145B with a flush of Greyed-Purple 185C. Lower Surface: Near RHS Yellow-Green 145B with a flush along margins of Greyed-Purple 185C.

REPRODUCTIVE ORGANS

Stamens:
*Number.*—35.
*Length.*—0.2 cm.
*Width.*—0.1 cm.
*Color.*—Near RHS Greyed-Purple 187A.

Pistil:
*Number.*—1.
*Length.*—0.4 cm.
*Style.*—Length: 0.2 cm. Color: Near RHS Yellow-Green 145D.

OTHER CHARACTERISTICS

Disease and pest resistance: Not observed to be susceptible nor resistant to normal diseases and pests of *Illicium floridanum.*
Temperature tolerance: USDA Zone 6.
Fruit/seed production: Star-like woody aggregate.

What is claimed is:

1. A new and distinct cultivar of *Illicium* plant named 'JCJC' as herein illustrated and described.

* * * * *